United States Patent [19]
Baldacci

[11] 4,313,952
[45] Feb. 2, 1982

[54] METHOD OF TREATING ACUTE ALCOHOLIC INTOXICATION WITH PYRIDOXINE P.C.A.

[76] Inventor: Massimo Baldacci, via delle Piagge 9, Pisa, Italy

[21] Appl. No.: 214,033

[22] Filed: Dec. 8, 1980

[30] Foreign Application Priority Data

Jun. 30, 1980 [IT] Italy .................. 23103 A/80

[51] Int. Cl.$^3$ .............................. A61K 31/44
[52] U.S. Cl. ............................................ 424/263
[58] Field of Search ........................................ 424/263

Primary Examiner—Stanley J. Friedman
Attorney, Agent, or Firm—Cushman, Darby & Cushman

[57] ABSTRACT

The treatment of patients suffering from acute alcoholic intoxication with pyridoxine 5-oxo-2-pyrrolidon-carboxylate permits the symptomatology of the psychomotor excitation and aggression to be readily and essentially completely solved.

2 Claims, No Drawings

METHOD OF TREATING ACUTE ALCOHOLIC INTOXICATION WITH PYRIDOXINE P.C.A.

BACKGROUND OF THE INVENTION

The present invention relates to a pharmaceutical composition for the treatment of acute alcoholic intoxication states.

Pyridoxine, also known as the vitamin $B_6$, is a well known active substance which found widespread use in several symptomatologies.

Among the uses which were proposed in the past, the treatment of acute alcoholic intoxication is included (wordworth V. P., Intravenous Detoxication of Drunkenness, Brit. Med. J. 935, 1953).

However such an application remained objectionable, since subsequent research work raised doubts about the efficacy of such a treatment (Gruber H. de, Mitteilung uber die Wirksamkeit von Vitamine $B_6$, bei Alcoholrausch, Munsh. Med. Wirschr., 96, 1445, 1954; Celice J. et al., Utilite du Pyridoxal (Vitamine $B_6$) dans le Traitement des Manifestations Neurologiques de l'Intoxication Alcoolique, Therapie, 14, 233/6, 1959).

Larcan, (Larcan et al, Le Traitement de l'Intoxication Alcoolique Oigne, Annales Medicales de Nancy, 1978, pag. 1159/1167), who for some time has used the pyridoxine for about 20 cases each week of acute ethylism, as treated by the mobile units (SOS Service), or hospitalized in the specialized section (isolated and excited patients), observed that the results are favourable as regards minor effects (space-time orientation, statics and equilibrium). Whereas inconstant results are obtained as regards psychomotor excitation.

DETAILED DESCRIPTION OF THE INVENTION

It has been now found, and is the subject of the present invention, that the administration, to patients suffering from acute alcoholic intoxication, of pyridoxine 5-oxo-2-pyrrolidon-carboxylate (pyridoxine P.C.A.) gives relevantly and unexpectably superior results with respect to the action obtainable with pyridoxine alone, especially as regards a ready reduction of the psychomotor excitation status and a rapid decrease in aggressive behavior.

As it is known, pyridoxine pyrrolidon-carboxylate, namely 5-oxo-2-pyrrolidon-carboxylate of 5-hydroxy-6-methyl-3,4-pyridine dimethanol, having the formula

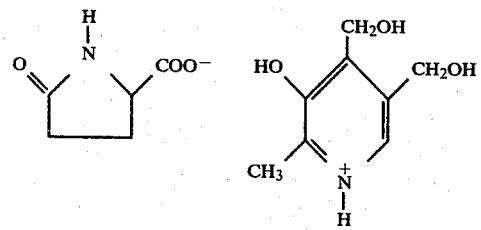

is a substance having moleculare weight 298.28 and melting point 96° to 98° C., which can be prepared in form of a crystalline white powder, odorless and of acidic taste, highly, soluble in water.

The pyridoxine P.C.A. in the past has been the subject of pharmacological testing, in view of several possible therapeutical uses, whereby the following data were assessed: $DL_{50}$, by i.v. route, in the mouse: 3480 mg/Kg $DL_{50}$, by i.p. route and per os, greater than the maximum administrable dose of 6 g/Kg.

The mutagenesis test (Ames test) and the teratogenesis test did not gave results suggesting objectionable effects. For the therapeutic use foreseen by the present invention, tests have been carried out with patients suffering from acute ethylism, by administering 300 mg of active substance (PCP) by the i.v. route.

For sake of comparison, an equivalent dose of pyridoxine hydrochloride (P) (250 mg by i.v. route) was administered to other patients, and the results are reported in the following table:

| Psychomotor excitation | | P Patients: 17 | | PCP Patients: 22 | |
|---|---|---|---|---|---|
| | | N. | % | N. | % |
| Rapid improvement | <1 h. | 2 | 11.8 | 9 | 40 |
| Slow improvement | <6 h. | 14 | 92 | 12 | 54.5 |
| worsening or persistence | | 1 | 5.7 | 1 | 4.5 |
| Aggressivity | | P Patients: 11 | | PCP Patients: 17 | |
| | | N. | % | N. | % |
| Ready improvement | <1 h. | 2 | 18.1 | 10 | 58.1 |
| Slow improvement | <6 h. | 9 | 81.8 | 7 | 41.1 |
| Worsening or persistence | | 0 | 0 | 0 | 0 |

In a double blind clinical study on patients suffering from chronic alcoholic intoxication, the results of the treatment with pyridoxine pyrrolidon-carboxylate (as tablets and vials) have been compared with those of equivalent dosages of pyridoxine administered in the corresponding pharmaceutical forms. The test was carried out on 30 male and 30 female patients, equally divided as regards the two preparations to be administered.

In each patient the hematochemical and enzymatic parameters (glycemia, azotemia, uricaemia, cholesterol, triglycerides, HB, He, EGT, OCT, S.G.O.T., S.G.P.T.) as well as the psychometric parameters (delayed memory, attention, efficiency, codification, effacement efficiency) were detected.

The statistical processing of the results revealed that both compounds are efficacious as regards the improvement of the neuropsychical and biohumoral symptomatology.

The pyridoxine pyrrolidon-carboxylate, particularly if parenterally administered, is significatively more active than pyridoxine.

In the experiments it has been possible to demonstrate, by testing on rats which were intoxicated for a week with 25% alcohol, that an inversion of the ratio ol and apoenzime of the tryptophan-pyrrolase oxygenase (T.P.O.). Under those conditions the pyridoxine pyrrolidone-carboxylate is significantly more active than pyridoxine as regards the stabilization of the apoenzyme.

The experiments with marked pyridoxine as regards the penetration of the coenzyme at the cellular level and the studies on the kinetics and on the distribution in the organs of the compound of the invention gave results which justify the higher therapeutic activity of the pyridoxine pyrrolidon-carboxylate with respect to the pyridoxine alone.

According to the research work of Prof. Rizza of the University of Catania (Italy) the labeled pyridoxine penetrates the hepatocytes in a ratio proportionally increasing as the amount of pyrrolydon-carboxylic acid (P.C.A.) added to the medium.

As revealed by the experiments, the radioactivity of the control cells, containing only $H_3$-pyridoxine, is relevantly higher, up to 8 times, in the presence of 10 $\mu$M of P.C.A.. Turning now to the pharmaceutical formulations of the composition according to the invention, some examples, having only illustrative but non limiting meaning are hereinafter reported.

1. Parenteral administration:
   5 ml vial containing a 6% solution of pyridoxine pyrrolid-don-carboxylate in apyrogenic water.
2. Oral administration:
   (a) Tablets containing:

| | | |
|---|---|---|
| pyridoxine pyrrolidon-carboxylate | mg | 300 |
| excipients, | q.s. to | 450 mg |
| (b) 15 ml vials containing: | | |
| pyridoxine pyrrolidon-carboxylate | mg | 150 |
| fructose | g | 6 |
| citric acid | g | 0.150 |
| water | q.s. to ml | 15 |
| (c) Powder formulation containing per each small envelope: | | |
| pyridoxine pyrrolidon-carboxylate | mg | 150 |
| citric acid | mg | 150 |
| sugar | q.s. to g | 5 |

I claim:
1. A method for the treatment of acute alcoholic intoxication and reducing psychomotor excitation and aggression, comprising administering to a person suffering therefrom pyridoxine pyrrolidone-carboxylate, by the parenteral or oral route in an amount sufficient to treat said intoxication and reduce said psychomotor excitation and aggression.
2. The method according to claim 1, wherein said amount, expressed in unit doses, is from 150 to 300 mg of pyridoxine pyrolidone carbonate.

* * * * *